US00PP16822P3

(12) United States Plant Patent
Carlson

(10) Patent No.: US PP16,822 P3
(45) Date of Patent: Jul. 18, 2006

(54) PERSIMMON TREE DENOMINATED DOC'S DELIGHT

(50) Latin Name: *Diospyros kaki*
Varietal Denomination: Doc's Delight

(75) Inventor: Arthur W. Carlson, McFarland, CA (US)

(73) Assignee: Arthur Carlson Family Ltd. Partnership, Porterville, CA (US)

( * ) Notice: Subject to any disclaimer, the term of this patent is extended or adjusted under 35 U.S.C. 154(b) by 0 days.

(21) Appl. No.: 10/863,063

(22) Filed: Jun. 7, 2004

(65) Prior Publication Data

US 2005/0273891 P1 Dec. 8, 2005

(51) Int. Cl.
*A01H 5/00* (2006.01)

(52) U.S. Cl. ..... Plt./156

(58) Field of Classification Search ..... Plt./156
See application file for complete search history.

*Primary Examiner*—Anne Marie Grunberg
(74) *Attorney, Agent, or Firm*—Worrel & Worrel

(57) ABSTRACT

A new and distinct variety of persimmon tree which is somewhat remotely similar to the Fuyu persimmon tree, but from which it is distinguished by producing fruit which are mature for harvesting and shipment approximately 10 days to 2 weeks prior to the fruit produced by the Fuyu persimmon tree and which is of larger size.

1 Drawing Sheet

Latin name of the genus and species of the plant claimed: *Diospyros kaki* L.
Variety denomination: Doc's Delight.

BACKGROUND OF THE NEW VARIETY

The present invention relates to a new and distinct variety of persimmon tree, which will hereinafter be denominated varietally as Doc's Delight, and, more particularly, to a persimmon tree which produces fruit, which are mature for commercial harvesting and shipment approximately the first week of October near Wasco in the southern San Joaquin Valley of California.

Commercial varieties of fruit trees may be distinguished, one from another, by a multiplicity of characteristics. Furthermore, there are many varieties of certain fruit trees while other types of fruit trees have only a few commercially recognized varieties. For example, peach trees have a plethora of recognized commercial varieties while persimmon trees have very few. Thus, in the case of persimmon trees, there are considerably fewer varieties from which to choose, of course both in the trees and the fruit therefrom. This makes new varieties of persimmon trees potentially of significantly more importance than is the case with peach trees. When this fact is coupled with all of the distinguishing characteristics, such as ripening date, size, coloration, flavor and the like, the commercial potential of such varieties may be significant.

The persimmon tree of the present invention appears to be a promising candidate in these regards, as will hereinafter be set forth in greater detail.

ORIGIN AND ASEXUAL REPRODUCTION OF THE NEW VARIETY

The persimmon tree of the present invention was discovered by the inventor in his persimmon orchard located near Wasco in the southern San Joaquin Valley of California. The inventor had planted about one thousand persimmon trees of the Fuyu variety in the orchard in 1991. In October 1996, the inventor discovered four (4) persimmon trees of the new variety of the present invention in the orchard as a sport of the Fuyu persimmon tree. The persimmon trees of the instant variety were readily distinguishable from the Fuyu persimmon trees in numerous respects including that they produced fruit which was ripe for commercial harvesting and shipment ten (10) to fourteen (14) days earlier that the fruit of the Fuyu persimmon trees.

In March 1997, at the inventor's direction, the persimmon tree of the instant invention was asexually reproduced by grafting bud wood of the new variety on to *Diospyros kaki* rootstock.

The inventor has closely watched the development of the asexually reproduced persimmon trees of the new variety since then and continues to observe the trees and has found them in all respects to be identical to the original trees of the subject invention.

SUMMARY OF THE INVENTION

The persimmon tree of the present invention is characterized by producing a large highly colored fruit, more specifically, of orange coloration which are ripe for commercial harvesting and shipment during the first week of October in the southern San Joaquin Valley of California. The new variety most closely resembles the Fuyu persimmon tree, from which it is derived, but from which it is distinguished in a number of respects including that the fruit thereof ripens ten to fourteen days earlier than the fruit of Fuyu persimmon tree and that the fruit of the instant variety is larger than that of the Fuyu persimmon tree.

BRIEF DESCRIPTION OF THE DRAWING

The accompanying drawing is a color photograph showing distinguishing characteristics of the new variety including fruit thereof with a first disposed in top plan view to display the stem end thereof with the calyx removed;

a second disposed bottom plan view to reveal the apex end thereof;

a third in side elevation; and a fourth severed along its transverse axis and laid open to reveal the flesh thereof with an absence of seeds.

Also shown is a terminal section of a branch of the new variety displaying upper and lower surfaces of the leaves.

DETAILED BOTANICAL DESCRIPTION

Referring more specifically to the pomological details of this new and distinct variety of persimmon tree, the following has been observed under the ecological conditions prevailing in the orchard of origin located near Wasco in the southern San Joaquin Valley of California. All major color code designations are by reference to the *Dictionary of Color*, by Maerz and Paul, First Edition, 1930. Common color names are also occasionally employed.

TREE

Generally: The persimmon tree is medium in size and trained to grow on a trellis.

*Size.*—Height, eight to ten feet.
*Size.*—Width, eight to ten feet when trained to grow on a trellis.
*Vigor.*—Good.
*Figure.*—Open vase, or open center system.
*Productivity.*—Very good.
*Regularity of bearing.*—Regular in typical climatic conditions in the southern San Joaquin Valley of California.

TRUNK

*Size.*—Medium, 38.1 cm (15 inches) to 50.8 cm (20 inches) in circumference at a point 45.72 cm (18 inches) above ground level.
*Surface texture.*—Moderately rough.
*Color.*—P1.56 J10 Catawba.
*Lenticels.*—Numbers — Moderate numbers.
*Lenticels.*—Size — Small, 5.08 cm (2 inches) in length.

BRANCHES

*Size.*—Medium, 22.86 cm (9 inches) to 25.4 cm (10 inches) in circumference at a point 38.1 cm (15 inches) above crotch.
*Surface texture.*—Slightly rough.
*Color.*—Mature branches — P1.55 E2 Mauve Castor.
*Color.*—Immature branches — P1.21 L8 — Shade of green, near gooseberry green.
*Angle of branches.*—45° at a point approximately 38.1 cm (15 inches) above crotch.
*Lenticels.*—Numbers — Moderate.
*Lenticels.*—Size — Small, 3.81 cm (1.5 inches) to 5.08 cm (2 inches) in length.

LEAVES

*Size.*—Generally — Medium to large, pinnately veined.
*Average length.*—125 mm (4.92 inches) to 150 mm (5.91 inches).
*Average width.*—72 mm (2.83 inches) to 90 mm (3.54 inches).
*Form.*—Ovate. Leaf tip is broadly acuminate.
*Color.*—Upwardly disposed surface — P1.22 L10 Brunswick Green.
*Color.*—Downwardly disposed surface — P1.20 E6 Grasshopper.
*Color.*—Leaf Vein — P1.17 L6. Shade of yellowish green.
*Marginal form.*—Entire.
*Leaf margin.*—Flat.
*Petiole.*—Size — Medium.
*Petiole.*—Length — 12 mm (0.47 inches) to 14 mm (0.55 inches).
*Petiole.*—Thickness — 3 mm (0.12 inches).
*Petiole.*—Color — P1.17 L6. Shade of yellowish green.
*Glands.*—None.
*Stipules.*—Length — Average 4 mm (0.16 inches).
*Stipules.*—Shape — Globular.
*Stipules.*—Color — P1.47 J8 Prune.

FLOWERS

Flower buds:

*Generally.*—Hardy in typical climatic conditions in the southern San Joaquin Valley of California. Flower buds are covered by large calyx.
*Size.*—Length — 11 mm (0.43 inches) to 15 mm (0.59 inches).
*Size.*—Width — 7 mm (0.28 inches).
*Surface texture.*—Smooth, glabrous.
*Color.*—P1.20 L9 Eden Green.
*Shape.*—Winged.
*Date of bloom.*—Less than 10% by April 23rd and 100% by mid May.
*Calyx.*—Flowery, not showy nor abundant.
*Calyx.*—Size — Large, 15 mm (0.59 inches) to 17 mm (0.67 inches).

Flowers:

*Size.*—Generally — Small to medium, 5 mm (0.2 inches) to 7 mm (0.28 inches).
*Petals.*—Number — Four (4).
*Petals.*—Form — Broadly ovate.
*Petals.*—Size — Length — Average 6 mm (0.24 inches) to 10 mm (0.39 inches).
*Petals.*—Size — Width — 5 mm (0.2 inches) to 7 mm (0.28 inches).
*Petals.*—Color — P1.10 I5 Mellow Glow.
*Petal claws.*—Absent.
*Flower pedicels.*—Medium.
*Flower pedicels.*—Length — 10 mm (0.39 inches) to 12 mm (0.47 inches).
*Flower pedicels.*—Thickness — 3 mm (0.12 inches).
*Flower pedicels.*—Color — P1.20 B6 Seaspray.
*Flower pedicels.*—Surface Texture — Glabrous.
*Calyx.*—Color — P1.20 Seaspray.
*Calyx.*—Surface Texture — Glabrous.
*Sepals.*—Number — Four (4).
*Sepals.*—Size — Large.
*Sepals.*—Length — 19 mm (0.75 inches).
*Sepals.*—Width — 16 mm (0.63 inches).
*Sepals.*—Surface Texture — Glabrous.
*Sepals.*—Form — Broadly ovate.
*Sepals.*—Color — P1.20 B6 Seaspray.
*Anthers.*—Size — Small, less than 1 mm.
*Anthers.*—Color — Light greenish brown.
*Stamens.*—Number — Eight (8), borne at base of flower petals.
*Stamens.*—Size — Very small, 2 mm (0.08 inches) to 4 mm (0.16 inches) long.

*Stamens.*—Color — Light green.
*Stamens.*—Surface Texture — Slightly pubescent.

FRUIT

Maturity when described: Ripe for commercial harvesting and shipment approximately the first week of October near Wasco, in the southern San Joaquin Valley of California.

*Size.*—Generally uniform and large for oriental persimmon.
*Average diameter in the axial plane.*—72 mm (2.83 inches) to 76 mm (2.99 inches).
*Average diameter transverse in the suture plane.*—51 mm (2.01 inches) to 52 mm (2.05 inches).
*Average diameter transverse and at right angles to the suture plane.*—73 mm (2.87 inches) to 78 mm (3.07 inches).
*Form.*—Globular shape with flat apex.
*Suture.*—Generally — Two (2) sutures at 90° angles to each other. The sutures are pronounced at top and middle of fruit, 2 mm (0.05 inches) deep, but only slightly indented at base of fruit.
*Stem cavity.*—Generally — Large.
*Stem cavity.*—Width — 22 mm (0.87 inches).
*Stem cavity.*—Depth — 8 mm (0.31 inches) to 10 mm (0.35 inches).
*Stem cavity.*—Length — 22 mm (0.87 inches).
*Stem cavity.*—Shape — Oval.
*Stem.*—Length — 13 mm (0.51 inches) to 17 mm (0.67 inches).
*Stem.*—Width — 4 mm (0.16 inches).
*Base.*—Rounded shape with flatness of blossom end.
*Pistil point.*—None.

Skin:

*Thickness.*—Average for persimmons.
*Texture.*—Glabrous.
*Tenacity.*—Adheres tightly to flesh.
*Tendency to crack.*—None observed.
*Color.*—Overall color at maturity develops at blossom end first and at maturity over 75–80% are fully colored.
*Blush color.*—P1.3 H10 Coral Bell.
*Ground color.*—P1.6 B9 Wood Rose Sorghum Brown. Absent on shoulder.
*Flavor.*—Sweet. Not astringent.

Flesh:

*Flesh color.*—Uniform throughout on the fruit, near the skin P1.3 H10 Coral Bell.
*Seeds.*—None.
*Color of seed cavities.*—P1.3 G10 Ember Glow.
*Flavor.*—Mild. No apparent astringency.
*Level of sweetness.*—Tree ripe fruit is sweet (16% soluble solids).
*Texture.*—Firm at commercial maturity.
*Ripening.*—Ripens first at blossom end.
*Eating quality.*—Similar to Fuyu variety.

Use: Fresh market.

Although the new variety of persimmon tree possesses the described characteristics noted above as a result of the growing conditions prevailing near Wasco, Calif. in the southern San Joaquin Valley of California, it is to be understood that variations of the usual magnitude and characteristics incident to changes in growing conditions, irrigation, fertilization, pruning, pest control, climatic variations and the like are to be expected.

Having thus described and illustrated my new variety of persimmon tree, what I claim as new and desire to be secured by Plant Letters Patent is:

1. A new and distinct variety of persimmon tree substantially as illustrated and described which is somewhat remotely similar to the Fuyu persimmon tree, but from which it is distinguished by producing fruit which are mature for commercial harvesting and shipment approximately the first week of October, or about 10 days to 2 weeks earlier than the fruit of the Fuyu persimmon tree, in the southern San Joaquin Valley of California and which has high coloration, large size and a very good flavor.

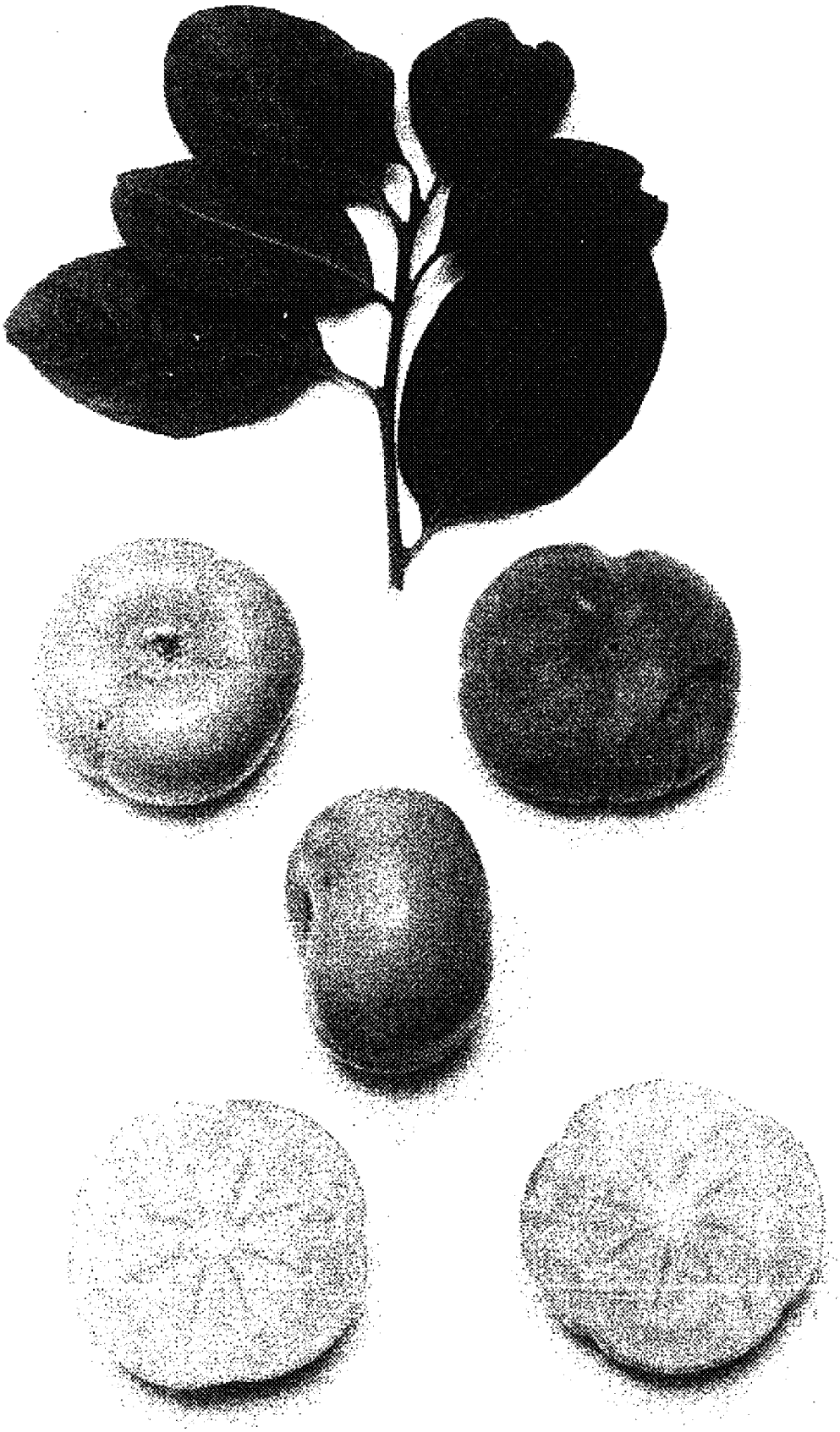

* * * * *